United States Patent [19]

Tam

[11] Patent Number: 4,622,960
[45] Date of Patent: Nov. 18, 1986

[54] INSTRUMENT FOR WIRE MANIPULATION IN BONE SURGERY

[76] Inventor: John W. Tam, 922 Fountain Springs La., Glendora, Calif. 91740

[21] Appl. No.: 742,518

[22] Filed: Jun. 7, 1985

[51] Int. Cl.[4] ............................................. A61F 5/04
[52] U.S. Cl. .............................. 128/92 VK; 128/92 R; 128/303 R
[58] Field of Search ............... 128/92 R, 92 E, 92 EC, 128/92 ED, 303 R

[56] References Cited

U.S. PATENT DOCUMENTS

| | | | |
|---|---|---|---|
| 3,381,685 | 5/1965 | Solbrig | 128/92 R |
| 4,531,517 | 7/1985 | Forte et al. | 128/92 R |
| 4,557,259 | 12/1985 | Wu | 128/92 E |
| 4,570,618 | 2/1986 | Wu | 128/92 E |

OTHER PUBLICATIONS

Stryker, "Depth Gauge", p. 33, Fracture Appliances Catalog, 1947.
Down Bros. & Meyer & Phelps Ltd., London, p. G67, "Orthopaedic Catalog", 20th Ed., May 18, 1966.

Primary Examiner—Gene Mancene
Assistant Examiner—C. W. Shedd
Attorney, Agent, or Firm—Boniard I. Brown

[57] ABSTRACT

A surgical instrument for manipulation of securement wire in small bone surgery has an elongated body section, a first end portion having a J-shaped hook at its end portion to engage wire to draw the wire through a passage, and a second end portion defining a notch to engage wire end portions for urging the same into a passage.

19 Claims, 14 Drawing Figures

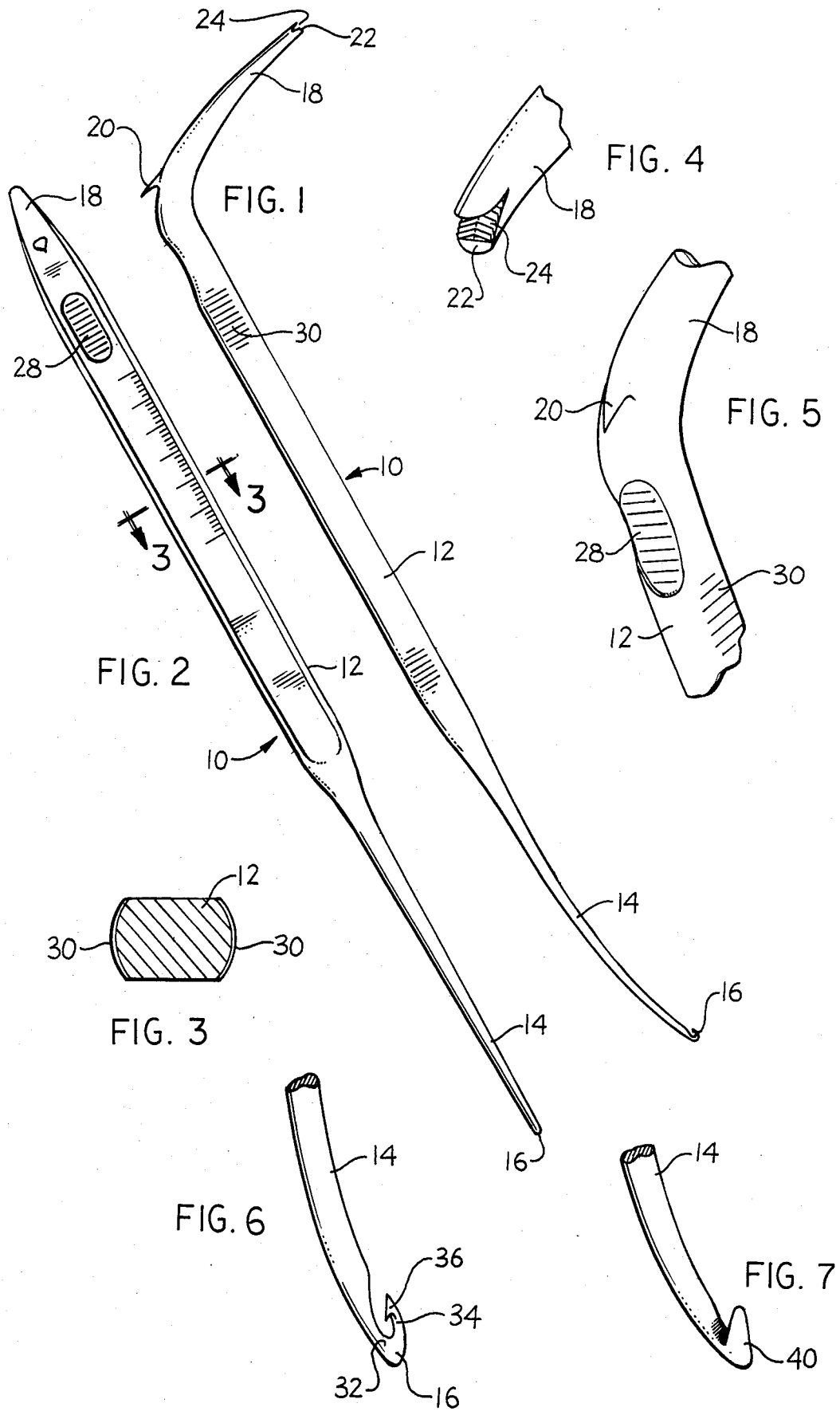

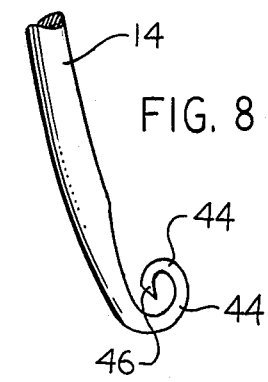
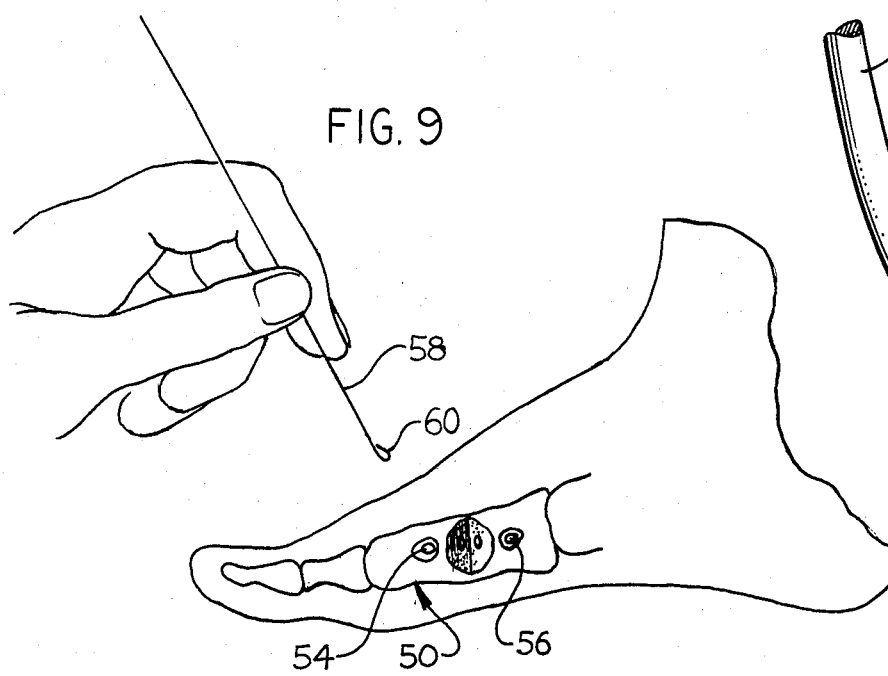
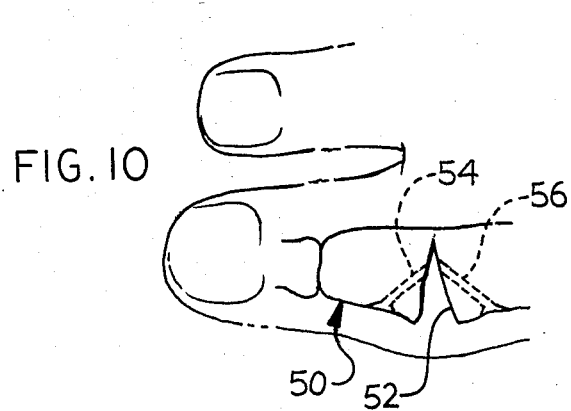
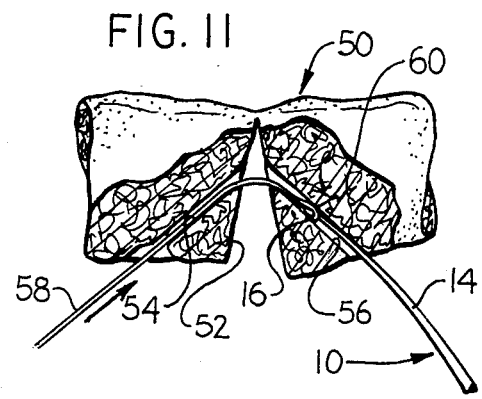
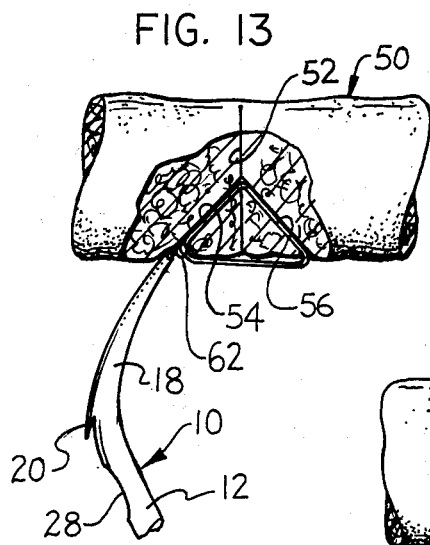
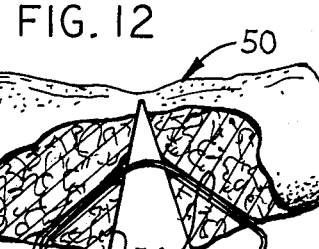
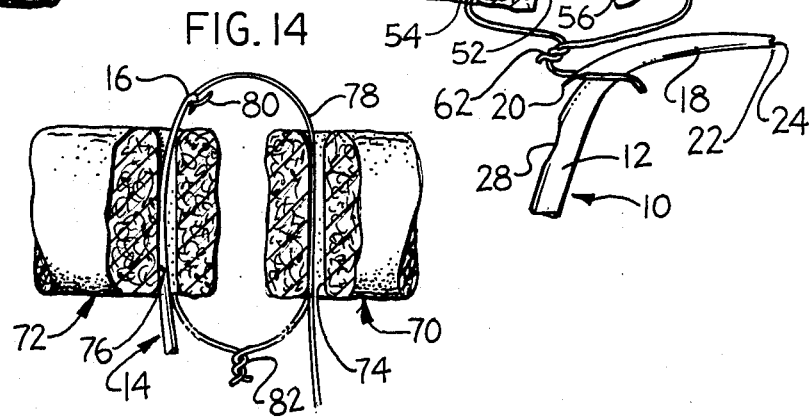

INSTRUMENT FOR WIRE MANIPULATION IN BONE SURGERY

BACKGROUND OF THE INVENTION

Surgical operations on small bones, such as bones of the feet, hands and small jaw bones, often require the threading or manipulating of securement wire through passages drilled in adjacent bone sections prior to securement together of the bone sections by the wire. An example of such surgery involving such manipulation of securement wire, is the operation on a foot bone to correct a bunion, which involves the removal of a V or pie shaped bone portion is cut away and the adjacent bone sections are secured together in order to reangulate the bone to eliminate the bunion to correct the malformation. Another example is that of a broken or fractured small bone, where it is desired to secure the bone sections together for healing, and where passages are drilled in adjacent bone sections, these passages ordinarily being parallel to the broken end faces of the bone sections.

In such surgical operations on small bones, a securement wire having a loop at its end, is extended through the passage in one of the bone sections. The opposite end portion of the securement wire must then be drawn through the passage in the other bone section by engagement of the loop on the wire and drawing the wire through the passage. The engagement of the securement wire end loop is generally required to be accomplished by feel and by "fishing", because any view of the loop and any engaging hook is blocked or obstructed by blood, tissue, etc. during surgery.

In the prior art, a conventional crochet hook has typically been utilized for extension through a passage to engage the loop at the end of the securement wire for pulling the wire through the passage. With the wire drawn through the passage, the end portions of the wire extending from the passages in the adjacent bone sections, are drawn together to secure together the adjacent bone sections, and the end portions of the wire are twisted together for securement. It is necessary or at least highly desirable, that the twisted end portions of wire be urged into one of the bone section passages where the wire end portions normally permanently remain after the healing together of the bone sections. The twisted wire end portions are thus countersunk into a passage, thus to eliminate any projection of wire to facilitate healing and prevent extension of wire end portions into tissue adjacent to the bone sections. If irritation or other problems should arise, the wire may later be removed, if necessary.

Crochet hooks and other expedients involve various disadvantages and shortcomings. They are inefficient and require excessive time for surgery. Securement wire frequently becomes disengaged from a hook not well-adapted to retain the same, with attendant delays, frustrations and complications during surgery. Such a device does not have a configuration or such relative angulation between its sections as to provide for effective use in handling during hooking of wire, pulling of wire through a passage or urging end portions of wire into a passage. No feature is provided to facilitate engagement of wire end portions for efficient urging thereof into a passage. No means are provided for engaging end portions of securement wire for twisting. The configurations of such devices is not adapted for effective grasping, prevention of undesired rotation in the hand, or sensing of orientation for delicate manipulations and movements. No scale is provided thereon for quick, accurate measurements of relative dimensions.

It is therefore an object of the present invention to provide a surgical instrument which eliminates or alleviates the foregoing disadvantages and shortcomings.

An object of the invention is to provide such an instrument which provides for efficient and effective securement wire manipulation during small bone surgery.

An object of the invention is to provide such an instrument which effectively engages and retains securement wire for manipulation during surgery.

An object of the invention is to provide such an instrument which is configurated to afford proper relative angulation of portions thereof for effective use in engaging and manipulating securement wire.

An object of the invention is to provide such an instrument wherein a notch is defined in an end portion for effective engagement with wire end portions for the efficient urging thereof into the end portion of a passage.

An object of the invention is to provide such an instrument which has barb means thereon to facilitate twisting of end portions of wire.

A further object of the invention is to provide such an instrument having configuration and features for effective, positive manual grasping and orientation sensing during surgery.

A further object of the invention is the provision of such an instrument having a scale for quick and convenient relative measurements.

SUMMARY OF THE INVENTION

The aforementioned objects and advantages of the invention are attained in a surgical instrument for the manipulation of securement wire in small bone surgery, which comprises an elongated body section, a first end section which has an end portion defining a generally J-shaped hook for engagement with the wire for withdrawal of the wire through a passage drilled in a bone section, and a second end section defining a notch in its end portion to engage the end portions of wire for the manual urging of these end portions into such passage. The first and second end sections are preferably tapered toward their end portions and have reduced outer end portions. The second end portion is preferably disposed at a substantial angle in relation to the body section. The outer end portion of the hook portion is pointed and preferably has a barb extending backward from the pointed portion. Flat body section surfaces are preferably provided for effective manual gripping and sensing of orientation of the instrument. A serrated indentation is preferably provided on the body section adjacent to the second end section, thus to provide improved thumb engagement and grasping for exerting force to urge wire end sections into a passage. The body section preferably has serrations for improved manual gripping during surgical manipulation. The body section may preferably bear scale indicia for bone measurements during surgery.

BRIEF DESCRIPTION OF THE DRAWINGS

FIG. 1 is a side elevational view of a preferred embodiment of the surgical instrument of the invention;

FIG. 2 is a plan view of the surgical instrument of FIG. 1;

FIG. 3 is a cross-sectional view taken at line 3—3 in FIG. 2;

FIG. 4 is a fragmentary perspective view of an end portion of the surgical instrument of FIG. 1;

FIG. 5 is a partial perspective view of a portion of the instrument of FIGS. 1 and 2, showing indentation and barb features according to the invention;

FIG. 6 is an enlarged perspective view of an end portion of the instrument of FIG. 1, showing a preferred form of hook feature according to the invention;

FIG. 7 is a view, similar to the view of FIG. 6, showing a modified form of hook utilized with the invention;

FIG. 8 is a view like that of FIGS. 6 and 7, showing another form of hook utilized with the invention;

FIG. 9 is an elevational view showing certain foot bones with a bone section removed and holes drilled in adjacent sections, in relation to a manually held securement wire having a looped end portion;

FIG. 10 is a partial plan or top view of a portion of the foot of FIG. 9;

FIG. 11 is an enlarged view of a portion of the bone of FIG. 10, showing securement wire extending through a passage in a bone section, and an end portion of an instrument of the invention extended into a passage in an adjacent bone section;

FIG. 12 is a view, generally like that of FIG. 11, showing securement wire extended through the passages in adjacent bone sections, with the wire end portions twisted together;

FIG. 13 is a view, generally similar to the view of FIG. 11, showing bone sections secured together by securement wire, with twisted wire end portions inserted in a bone passage by an end portion of the instrument of the invention; and FIG. 14 is an elevational view of adjacent broken bone sections, showing transverse passages drilled therein and securement wire extended therethrough, with an end portion of an instrument according to the invention inserted in one of the passages and drawing securement wire therethrough.

DESCRIPTION OF THE PREFERRED EMBODIMENT

FIGS. 1 through 6 illustrate a preferred embodiment of a surgical instrument 10 for securement wire manipulation, according to the invention. The instrument comprises an elongated central body section 12, a tapered reduced first end section 14 defining at its end a wire-engaging hook 16, and a second end section 18 extending at a substantial angle of approximately 75°–80° relative to body section 12. The second end section extends from its curved connection with body section 12 and defines a barb 20 (FIGS. 1 and 5) for a purpose hereinafter described. End section 18 has an end face 22 and a generally V-shaped notch 24 extending inwardly from this end face, as best shown in FIG. 4, one portion of the end section defining the notch being thicker than the other, as shown. Flat upper and lower instrument surfaces, shown in FIGS. 1, 2 and 3, provide good, positive manual grasp during operations and manual indication and sensation of instrument orientation.

A serrated indentation or recess 28 is defined in the upper surface of the body section 12 adjacent to end section 18 for improved thumb grip and engagement during operation of the instrument in manipulating wire during surgery. A plurality of serrations 30 along the side surfaces of the instrument, as indicated in FIGS. 1 and 5, provide for improved manual grasping to prevent slipping, particularly when the instrument is wet and slippery because of blood and body fluids during surgery.

A preferred form of the hook end portion 16 is shown in FIG. 6, and includes a deep U-shaped recess 32 and an arm 34 on which is defined a barb 36 having a point extending in the direction opposite from the extension of arm 34 to retain the wire in recess 32.

FIG. 7 shows a modified or simplified form of hook 40. FIG. 8 shows another modified form of hook 42 having a curved arm 44 and including a reverse extension 46, thus defining a hook of generally "e" shaped configuration, as shown, thus better to retain a securement wire utilized with the invention, without disengagement.

FIGS. 9 through 13 illustrate the utilization of the instrument of the invention in surgical operations on small bones, such as those in the foot or hand of the person. FIGS. 9 and 10 show certain bones of the human foot, with a bone 50 to be angulated having a V-shaped portion of bone removed to define a V-shaped notch 52. Openings or drilled passages 54, 56 are defined at the angles shown in the adjacent bone portions for extension therethrough of a securement wire 58. FIG. 11 shows securement wire 58 inserted through one of the passages 54, and end section 14 of the instrument is inserted through the passage 56 in the other bone portion during an operation, for the purpose of engaging the hook 16 at the end of instrument section 14 in a loop 60 at the end of the securement wire. Such engagement must generally be effected by feel, because of the lack of visibility due to obstruction, by blood, etc., during surgery. Once the hook 16 is engaged in the wire loop 60, the wire is drawn outwardly through passage 56. The end portions of the wire are then twisted together, as indicated at 62 in FIG. 12, barb 20 on the instrument providing good engagement with the wire to commence and facilitate manual twisting of the wire end portions. With the wire end portions thus twisted together, the instrument is manipulated to urge end portion 18, with the wire engaged in notch 24, into the outer portion of passage 54, as shown in FIG. 13.

FIG. 14 shows a different type of small bone separation wherein two adjacent bone sections 70 and 72 are broken or separated, and have been drilled to define transverse passages 74, 76 in the adjacent bone sections. A securement wire 78 is inserted through one of the passages, and instrument end portion 14 is inserted through the other passage, its hook 16 engaging in the loop 80 at the end of the wire. The wire is then pulled through the other passage 76. The end portions of the wire are then twisted together, as indicated at 82, and the twisted wire end portions are urged into the passage in the general manner as indicated in FIG. 13.

Thus there has been shown and described a novel instrument which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

The inventor claims:

1. A surgical instrument for manipulation of securement wire in small bone surgery wherein adjacent bone sections are drilled to define passages for extension of the wire therethrough, said surgical instrument comprising:
   an elongated body section,
   a first end section having an end portion defining a generally J-shaped hook for engagement with the wire for withdrawal of the wire through one of the passages, and
   a second end section having an end portion defining a notch for engaging wire end portions for manual urging of the end portions into one of the passages.

2. A surgical instrument according to claim 1 wherein:
   the first and second end sections are tapered and have reduced outer end portions.

3. A surgical instrument according to claim 2, wherein:
   said second end portion is disposed at a substantial angle relative to said body section.

4. A surgical instrument according to claim 2, wherein:
   the outer end portion of said hook portion is pointed.

5. A surgical instrument according to claim 4, wherein:
   said hook outer end portion has a barb thereon extending backward from said end pointed portion.

6. A surgical instrument according to claim 2, wherein:
   said body section has flat surfaces for manual gripping and manual sensing of orientation of the instrument.

7. A surgical instrument according to claim 1, wherein:
   said second end portion is disposed at a substantial angle relative to said body section.

8. A surgical instrument according to claim 7, wherein:
   the outer end portion of said hook portion is pointed.

9. A surgical instrument according to claim 7, wherein:
   said body section has flat surfaces for manual gripping and manual sensing of orientation of the instrument.

10. A surgical instrument according to claim 7, wherein:
    said body section defines an indentation adjacent to the second end section for improved thumb engagement and grasping.

11. A surgical instrument according to claim 7, wherein:
    said body section has serrations thereon for improved manual gripping during surgical manipulation.

12. A surgical instrument according to claim 1, wherein:
    the outer end portion of said hook portion is pointed.

13. A surgical instrument according to claim 12, wherein:
    said hook outer end portion has a barb thereon extending backward from said end pointed portion.

14. A surgical instrument according to claim 1, wherein:
    said body section has flat surfaces for manual gripping and manual sensing of orientation of the instrument.

15. A surgical instrument according to claim 14, wherein:
    said body section bears indicia defining a scale for bone measurements during surgery.

16. A surgical instrument according to claim 1, wherein:
    said body section defines an indentation adjacent to the second end section for improved thumb engagement and grasping.

17. A surgical instrument according to claim 16, wherein:
    said body section has serrations thereon for improved manual gripping during surgical manipulation.

18. A surgical instrument according to claim 1, wherein:
    said body section has serrations thereon for improved manual gripping during surgical manipulation.

19. A surgical instrument according to claim 1, wherein:
    said body section bears indicia defining a scale for bone measurements during surgery.

* * * * *